United States Patent [19]

Sasaki et al.

[11] Patent Number: 5,489,303
[45] Date of Patent: Feb. 6, 1996

[54] BIOCOMPATIBLE MATERIAL FOR MEDICAL APPARATUS COMPRISING HYDROPHOBICALLY BOUND OIL-SOLUBLE VITAMIN

[75] Inventors: Masatomi Sasaki; Hiroki Sakakibara; Makoto Saruhashi; Shinichi Tategami, all of Ashigarakami, Japan

[73] Assignee: Terumo Kabushiki Kaisha, Tokyo, Japan

[21] Appl. No.: 200,569

[22] Filed: Feb. 22, 1994

Related U.S. Application Data

[63] Continuation of Ser. No. 825,270, Jan. 24, 1992, abandoned.

[30] Foreign Application Priority Data

Jan. 25, 1991 [JP] Japan ................................. 3-0087147

[51] Int. Cl.⁶ ..................... A61F 2/02; A61F 2/06
[52] U.S. Cl. ................. 623/11; 623/1; 604/266; 424/422; 424/423
[58] Field of Search ........................ 623/1, 11, 66; 424/422, 423; 604/266

[56] References Cited

U.S. PATENT DOCUMENTS

| 4,588,407 | 5/1986 | Isono et al. ........................ 623/11 |
|-----------|--------|----------------------------------------------|
| 4,722,906 | 2/1988 | Guire ................................. 436/501 |
| 5,217,492 | 6/1993 | Guire et al. ......................... 623/11 |

FOREIGN PATENT DOCUMENTS

| 0103816 | 9/1983 | European Pat. Off. .............. 1/3 |
| 0335972 | 11/1987 | European Pat. Off. . |
| 0404683 | 6/1990 | European Pat. Off. . |

OTHER PUBLICATIONS

Alberts et al., Molecular Biology of the Cell, Garland Pub. Inc., (1983), pp. 91–96.

Sheeler et al, Cell Biology: Structure, Biochemistry and Function, John Wiley & Sons, (1980), p. 90.

"Medical Materials and Organism," pp. 36–37 and 289–290, Kodansha Scientific, (with English translation).

*Primary Examiner*—Paul B. Prebilic
*Attorney, Agent, or Firm*—Burns, Doane, Swecker & Mathis

[57] ABSTRACT

A medical material which comprises an oil-soluble vitamin hydrophobically bound to a hydrophobic moiety containing macromer which is bound to the surface of a polymeric substrate via a copolymer is described. Suitable macromers include for example glycidyl methacrylate-linoleic acid. Suitable polymeric substrate materials include, in particular, cellulose. Methods for producing said medical material are also provided.

9 Claims, 1 Drawing Sheet

BIOCOMPATIBLE MATERIAL FOR MEDICAL APPARATUS COMPRISING HYDROPHOBICALLY BOUND OIL-SOLUBLE VITAMIN

This application is a continuation of application Ser. No. 07/825,270, filed Jan. 24, 1992, now abandoned.

BACKGROUND OF THE INVENTION

Field of the Invention

This invention relates to a medical material, a method for the production thereof, and a medical apparatus which stably exhibits high biocompatiblility and excellent safety for a long time.

In recent years, artificial internal organs such as artificial kidneys, artificial lungs, and blood separating devices have been produced and put to use. The materials of which these artificial internal organs are formed are required to possess excellent biocompatiblility. Use of an artificial internal organ destitute of biocompatibility is highly dangerous because the contact of the material thereof with blood or vital tissue has the possibility of injuring hemocytes in the blood and inducing the formation of plasma protein and thrombosis. For the impartation of biocompatibility to the materials forming artificial internal organs, therefore, various methods for reformation have been heretofore proposed.

Particularly the practice of effecting graft polymerization by the use of a macromer has been recently in vogue. The formation of a graft copolymer, for example, has been attained by copolymerizing the macromer of a methacrylic ester with 2-hydroxyethyl methacrylate. It has been known that this graft copolymer has a better antithrombic property than countertype homopolymers and random copolymers ("Medical Materials and Organism," page 37 and pages 287 to 289, compiled by Yukio Imanish et al. and published by Kodansha Scientific K.K., 1982). In the graft copolymer produced by this polymerization of a macromer with other monomer, the graft chain is formed not only on the surface of the polymer but in the interior of the polymer. The graft copolymer, therefore, has the problem of introducing a change in the internal quality of the polymer.

The method for enhancing the biocompatibility of a medical material by physically coating this material on the surface with an oil-soluble vitamin has been known to the art (U.S. Pat. No. 4,588,407, for example). The medical material having the surface thereof coated with the oil-soluble vitamin brings about a secondary effect sparingly on organisms and avoids causing any transient decrease in leukocyte. The coating of an oil-soluble vitamin deposited only physically on the surface of the material, however, exhibits to the substrate material such a weak binding force as to entail possible migration of the vitamin into the blood.

This invention, therefore, has as an object thereof the provision of a novel medical material and a method for the production thereof.

Another object of this invention is to provide a medical material which exhibits high biocompatibility stably for a long time and which also excels in safety.

SUMMARY OF THE INVENTION

The objects described above are accomplished by a medical material produced by depositing an oil-soluble vitamin through the medium of a macromer containing a hydrophobic moiety on the surface of a substrate formed of a functional group-containing polymer.

The macromer mentioned above is preferable to be bound to the surface of the substrate through the medium of a copolymer containing a reactive group capable of forming a covalent bond with the functional group of the polymer mentioned above. The hydrophobic moiety mentioned above is preferable to be selected from the group consisting of a fluorine side chain, a silicone side chain, and an alkyl side chain. The average molecular weight of the hydrophobic moiety is preferable to be in the range of from 100 to 5,000.

The objects are also accomplished by a method for the production of a medical material, which comprises a first step of forming a covalent bond between the functional group of a macromer and part of the reactive group of a copolymer, a second step of forming a covalent bond between part of the reactive group of the copolymer and the functional group of the polymer, and a third step of causing an oil-soluble vitamin to contact and deposit fast on the hydrophobic moiety of the macromer.

The objects are further accomplished by a medical apparatus of which at least the portions destined to contact blood are formed of the medical material set forth in any of the preceding paragraphs describing the objects of this invention.

The objects are further accomplished by a medical material produced by causing at least one member selected from the group consisting of higher alcohols and higher alcohol macromers to be bound either directly or through the medium of a polymer to a substrate.

Since the medical material of this invention is enabled to retain, in the presence of water, an oil-soluble vitamin on the surface of the substrate thereof by virtue of a hydrophobic interaction as described above, it is capable of manifesting stable biocompatibility and excellent safety for a long time without inducing liberation of the oil-soluble vitamin.

The hydrophobic interaction can also be referred to as a hydrophobic bond since the water present in a biological fluid effectively forces the hydrophobic groups together.

When the macromer mentioned above is formed by being bonded to the surface of the substrate through the medium of a copolymer containing a reactive group capable of forming a covalent bond with the functional group of the aforementioned polymer, it can change the surface property of the substrate without causing any change in the internal property of the substrate because the hydrophobic moiety of the macromer is formed only on the surface of the substrate and not in the interior of the polymer. Since the macromer allows a multiplicity of oil-soluble vitamins to be retained at one point of bonding of the polymer, the medical material is enabled to manifest high biocompatibility.

Further, the medical material of this invention can be stably manufactured because it uses a higher alcohol and, as a result, the reaction which proceeds during the manufacture does not easily entail a secondary reaction or decomposition. Moreover, the activation of the complement system is curbed and the substrate is vested with lasting stable biocompatibility because a higher alcohol and/or a higher alcohol macromer is bound to the substrate directly or through the medium of a polymer.

EXPLANATION OF THE PREFERRED EMBODIMENT

Figure 1:
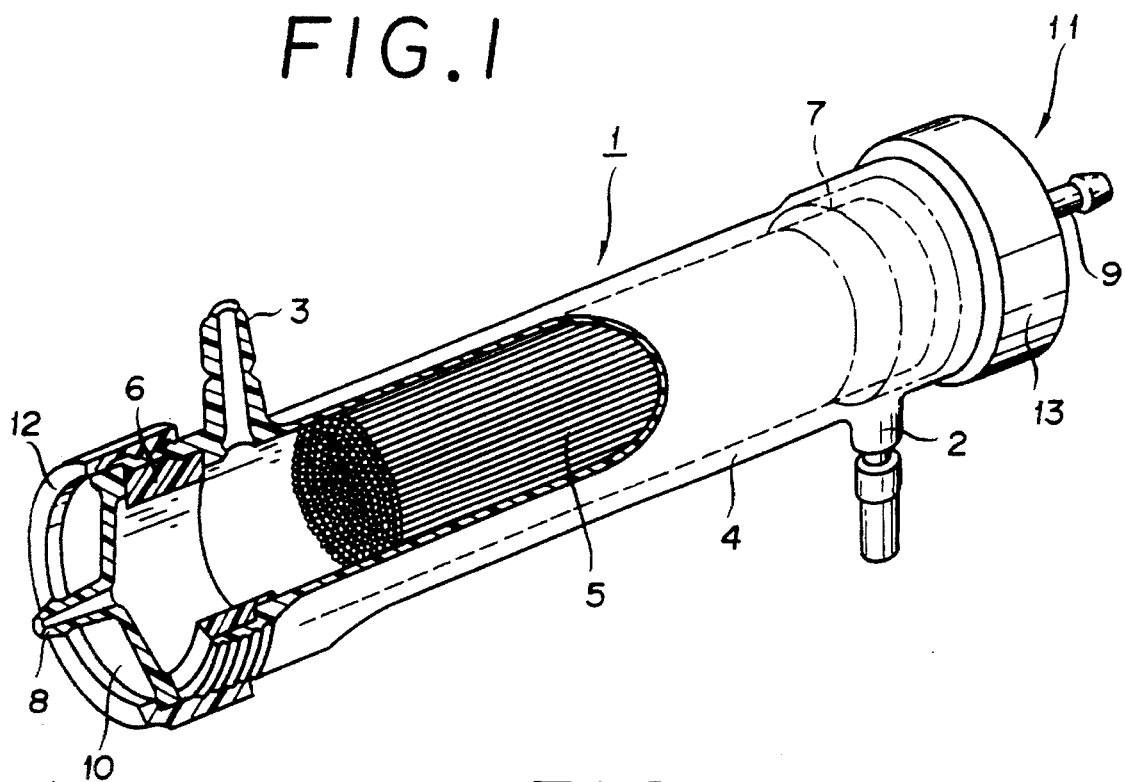
FIG. 1 is a partially cutaway perspective view illustrating the construction of a dialyzer using a medical material of this invention.
Figure 2:
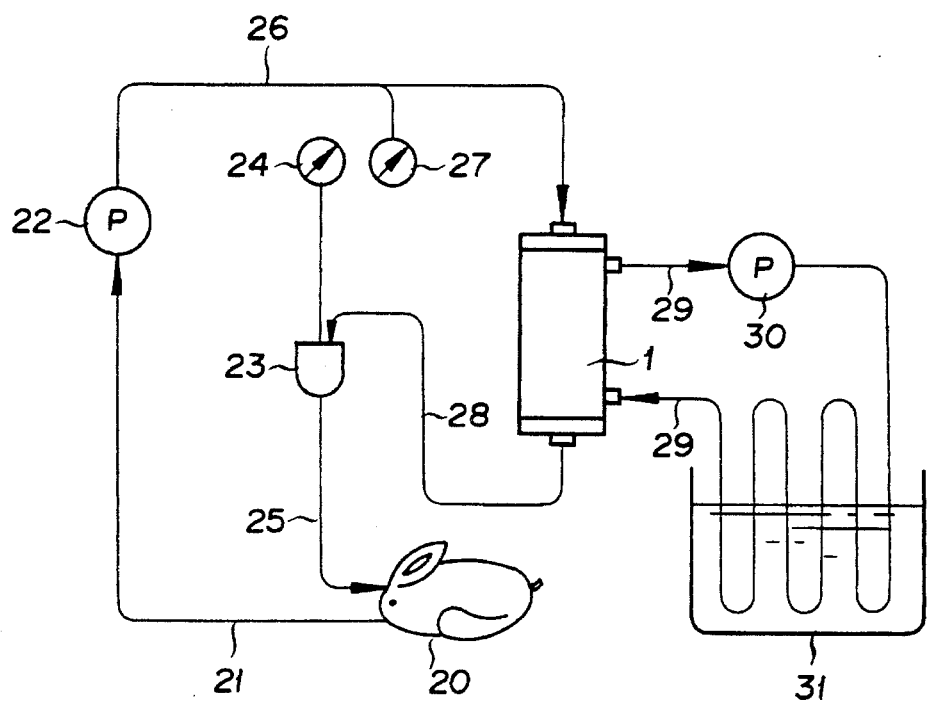
FIG. 2 is a diagram illustrating an experimental circuit for extracorporeal circulation for the dialyzer.

Now, this invention will be described in detail below.

The oil-soluble vitamins which are effectively usable in this invention include vitamins A, vitamins D, vitamins E, vitamins K, and ubiquinones, for example.

The vitamins A include vitamins A such as retinol (vitamin $A_1$ alcohol), retinal (vitamin $A_1$ aidehyde), vitamin $A_1$ acid, 3-dehydroretinol (vitamin $A_2$ alcohol), and 3-dehydroretinal (vitamin $A_2$ aidehyde) and provitamins A such as beta-carotene (beta, beta-carotene), alpha-carotene (beta, epsilon-carotene) and gamma-carotene (beta, psi-carotene), for example.

The vitamins D include vitamins D such as vitamin $D_2$, vitamin $D_3$, vitamin $D_4$, vitamin $D_5$, vitamin $D_6$, and vitamin $D_7$ and provitamins thereof, for example.

The vitamins E include tocopherols such as α-tocopherol, β-tocopherol, γ-tocopherol, and δ-tocopherol and tocotrienols such as α-tocotrienol, β-tocotrienol, γ-tocotrienol, and δ-tocotrienol, for example.

The vitamins K include vitamin $K_1$ and vitamins $K_2$, for example.

The ubiquinones include ubiquinone-1 to ubiquinole-12 (Q-1 to Q-12) and the oxidized forms thereof and amino chloride compounds thereof, for example.

The medical material of this invention is characterized by having such an oil-soluble vitamin deposited through the medium of a macromer containing a hydrophobic moiety on the surface of a substrate formed of a functional group-containing polymer.

In the medical material of this invention, the polymer of which the substrate is formed has no particular restriction except for the sole requirement that it should possess repeating units containing a functional group. The functional groups which the repeating unit are allowed to contain include hydroxyl group, amino group, carboxyl group, epoxy group, and aidehyde group, for example. As polymers possessing a hydroxyl group as the functional group, regenerated cellulose and cellulose derivatives may be cited. In the unit of regenerated cellulose shown below, for example, the hydroxyl group indicated by an asterisk (*) is a functional group. Incidentally, the hydroxyl group not indicated by an asterisk (*) and attached to the 3 position possesses poor reactivity from the standpoint of the construction of cellulose.

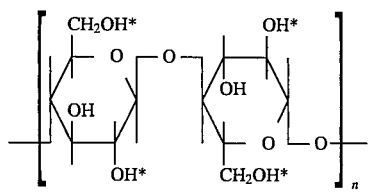

The other polymers which are effectively usable herein include polyvinyl alcohol, partially saponified polyvinyl acetate, ethylene-vinyl alcohol copolymers, partially saponified ethylene-vinyl acetate polymers, polyacrylic acid and polymethacrylic acid and copolymers thereof, polyhydroxy methacrylate, chitin, chitosan, collagen, and polyacrylamide, for example. The term "macromer" as used in this invention refers to a macromolecular compound containing a reactive functional group.

The hydrophobic moiety has no particular restriction except for the requirement that it should be capable of retaining the oil-soluble vitamin by a hydrophobic interaction. The hydrophobic moieties which are usable herein include a fluorine type side chain such as of perfluoroalcohol, a silicone type side chain such as of polydimethyl siloxane derivative, fatty acids, fatty acid derivatives, higher alcohols, and alkyl type side chains such as of higher alcohol derivatives, for example. The average molecular weight of this hydrophobic side chain is desired to be in the range of from 100 to 5,000. If the average molecular weight is less than 100, the oil-soluble vitamin cannot be retained with sufficient fastness. Conversely, if the average degree of polymerization exceeds 5,000, the hydrophobic moiety has the possibility of altering the nature of the polymer itself of the substrate.

The macromer containing the hydrophobic moiety of the nature described above is caused to assume a flexible linear structure containing neither a cyclic structure nor a triple bond. Owing to the assumption of this particular structure, the macromer is enabled to be bound in an amply mobile and stable state to the surface of the substrate.

Preferably, the macromer containing the hydrophobic moiety is bound through the medium of a spacer to the copolymer which will be described more specifically hereinbelow.

The spacers which are effectively usable herein include alkylene glycol diamines such as polyethylene glycol diamine, polypropylene glycol diamine, and polytetramethylene glycol diamine, for example.

The average degree of polymerization of the alkylene glycol diamine is preferable to be approximately in the range of from 1 to 100, though it is variable with the kind of the alkylene.

In this invention, the macromer containing the hydrophobic moiety (hereinafter the "macromer" will be occasionally construed in a broad sense of the word such as to embrace the spacer) is preferable to be formed by being bound to the surface of the substrate through the medium of a copolymer containing a reactive group capable of forming a covalent bond with the functional group of the polymer of which the substrate is formed.

The copolymer serving as the medium has no particular restriction except for the requirement that it should contain a reactive group capable of forming a covalent bond with the functional group of the polymer as described above. As the reactive group, the copolymer is an epoxy group, a carboxyl group, a group of the ester thereof, and/or an aidehyde group. The copolymer and the hydrophobic moiety mentioned above can be bound to each other by graft copolymerizing the hydrophobic moiety through the medium of the epoxy group of the copolymer, for example.

The monomer as the raw material for the copolymer containing an epoxy group is preferable to be the glycidyl ester of a (meth)acrylic acid. The monomer as the raw material for the copolymer containing a carboxyl group is preferable to be a (meth)acrylic acid. The raw materials which are effectively usable as the raw material for the copolymer include esters such as (meth)acrylic esters represented by methyl (meth)acrylates, ethyl (meth)acrylates, propyl (meth)acrylates, isopropyl (meth)acrylates, butyl (meth)acrylates, isobutyl (meth)acrylates, hydroxyethyl (meth)acrylates, and mixtures thereof, for example.

The use of a polymerization initiator such as, for example, ammonium eerie nitrate or ferrous salt of hydrogen peroxide suffices to produce the copolymer from the aforementioned monomer. The weight ratio of the epoxy group-containing monomer to the copolymer preferably ranges from 0.01 to 60% by weight, preferably from 1 to 10% by weight.

The average molecular weight of the copolymer is preferably approximately in the range of from 500 to 500,000, preferably from 5,000 to 100,000.

In this invention, the amount of the macromet and that of the oil-soluble vitamin relative to the amount of the substrate are preferably respectively in the range of from 1 to 200 parts by weight and range of from 1 to 1900 parts by weight, preferably in the range of from 20 to 150 parts by weight and the range of from 50 to 500 parts by weight, based on 100 parts by weight of the substrate.

Now, the method for the production of the medical material of this invention will be described below.

To be specific, the method for the production of the medical material of this invention is characterized by comprising a first step of forming a covalent bond between the functional group of a macromer and part of the reactive group of the copolymer, a second step of forming a covalent bond between part of the reactive group of the copolymer and the functional group of the polymer, and a third step of causing an oil-soluble vitamin to contact and deposit fast on the hydrophobic moiety of the macromer.

For example, the copolymer is dissolved in a solvent containing acetone, carbon tetrachloride and acetonitrile at room temperature, a dehydrating condensing agent such as N, N'-dicyclohexylcarbodiimide (1.2 mol per 1 mol of a carboxyl group of the copolymer) is added at a room temperature, the macromer 0.25 mol of an amino group of the macromer per 1 mol of a carboxyl group of the copolymer) is added, and is maintained at a temperature of 80° C. for 30 minutes. Then in order to remove an unnecessary component (in such case, it is N, N'-dicyclohexyl urea), the mixture is cooled in an iced water for 30 minutes to precipitate and the precipitate is filtered off. Then in order to remove an unreacted macromer, water (10 times of the solvent) is added to the filtrate because the unreacted macromer dissolves in water and is subjected to centrifugation at 10,000 r.p.m. for 5 minutes.

The covalent bond between the functional group of the macromer and the reactive group of the copolymer can be formed by any of the known methods available for this purpose.

The formation of a covalent bond between the polymer forming the substrate and the product of union of the macromer and the copolymer obtained by the method described above (hereinafter referred to as a "macromolecular derivative") is effected by dissolving the macromolecular derivative in a suitable organic solvent, adding a Lewis acid catalyst and/or a basic catalyst to the resultant solution, and establishing contact between the polymer and the macromolecular derivative as by immersing the polymer in the solution. The amount of the catalyst is in the range of from 0.01 to 20% by weight, preferably from 0.5 to 5% by weight. The temperature of the reaction is in the range of from 10° to 300° C., preferably 20° to 150° C.

The Lewis acid catalysts which are effectively usable herein include boron trifluoride, tin tetrachloride, and zinc chloride, for example. The basic catalysts which are effectively usable herein include hydroxides of alkaline earth metals, particularly calcium, strontium, barium, and radium and hydroxides of alkali metals such as lithium hydroxide, potassium hydroxide, rubidium hydroxide, cesium hydroxide, and francium hydroxide, for example.

The organic solvents which are effectively usable herein include dioxane, acetone, diethyl ketone, methy ethyl ketone, ethyl acetate, isoamyl acetate, tetrahydrazine, and the like. The concentration of the macromolecular derivative in the solution is in the range of from 0.01 to 40% by weight, preferably from 0.1 to 10% by weight.

Then, the solution of an oil-soluble vitamin in an organic solvent is brought into contact with the resultant modified polymer. The concentration of the oil-soluble vitamin solution to be used is approximately in the range of from 0.05 to 20 w/v %, preferably from 0.5 to 5 w/v %. The time of contact of the solution to the modified polymer is approximately in the range of from 30 seconds to 60 minutes, preferably from 30 seconds to 5 minutes. After this contact is completed, the retention of the oil-soluble vitamin to the modified polymer is attained by introducing an inert gas to the oil-soluble vitamin at a temperature in the range of from 10° to 80° C. preferably from 15° to 25° C. thereby expelling the organic solvent. The organic solvents which are effectively usable herein include alcohols such as methanol, ethanol, n-propanol, isopropanol, n-butanol, and isobutanol, ethers such as diethyl ether and tetrahydrofuran, and Freon solvents such as 1,1,2-trichloro- 1,2,2-trifluoroethane, for example. The medical material consequently produced is sterilized by the treatment with an autoclave, ethylene oxide, gamma ray, for example, before it is put to actual use.

Now, the medical apparatus of this invention will be described below.

To be specific, the medical apparatus of this invention is constructed so that at least the portions thereof destined to contact blood are formed of the medical material described above. As typical examples of the medical apparatus, extracorporeal circulation systems such as artificial lung circuit systems, artificial dialysis systems, blood plasma separation systems, and various catheters and artificial organs such as artificial blood vessels which are buried in human bodies may be cited. The medical apparatus of this invention precludes the liberation of the oil-soluble vitamin for a long time and manifests stable biocompatibility and excellent safety because at least the portions of the apparatus destined to contact blood are formed of the medical material described above.

Further, since the medical apparatus of this invention is so constructed that a higher alcohol and/or a higher alcohol macromer is bound directly or through the medium of a polymer to the substrate, it enjoys prominent biocompatibility originating in the higher alcohol. Since the hydroxyl group of the higher alcohol reacts with the functional group of the substrate or the polymer to give rise to an ether bond therebetween, the bond in the medical apparatus is stronger than the ester bond resulting from the reaction of the carboxyl group as the reactive terminal of a fatty acid with the functional group of the substrate or the polymer. This fact explains why the medical apparatus of this invention exhibits lasting stable biocompatibility without entailing liberation of the higher alcohol.

The hydroxyl group of a higher alcohol is used for the production of a higher alcohol macromer, the bond can be easily formed by the addition polymerization of a molecular chain (spacer) under the conditions incapable of readily inducing a secondary reaction.

The use of a higher alcohol macromer enables the medical apparatus to curb the adhesion of blood platelets by virtue of the interposition of a molecular chain (spacer) between the higher alcohol and the substrate or the polymer, acquire high biocompatibility, obtain easy control of the molecular chain length, and ensure stable mobility of the molecular chain.

The higher alcohol in this invention is preferable to be a monohydric alcohol from the standpoint of adjustment of the molecular chain and manufacture of the medical material. The alcohol is preferable to be in an unsaturated form in point of resistance to thrombosis. To be specific, the higher alcohols having 4–30 carbon atoms, preferably 10–20 carbon atoms which are effectively usable herein include oleyl alcohol, lauryl alcohol, myristyl alcohol, cetyl alcohol, and stearyl alcohol, for example. Among other alcohols, oleyl alcohol proves to be particularly desirable in point of compatibility for blood.

In this invention, for the purpose of enhancing the biocompatibility, particularly the adaptability for blood, the higher alcohol may be bound in the form of a higher alcohol macromer preferably through the medium of a hydrophilic spacer.

As a typical spacer, an alkylene glycol having highly reactive functional groups attached one each to the opposite terminals thereof may be cited. The alkylene glycols which answer this description include polyethylene glycol diamine, polypropylene glycol diamine, and polytetramethylene glycol diamine, for example.

When the spacer to be used has an alkylene glycol sheleton, for example, the degree of polymerization thereof is preferable to be approximately in the range of from 1 to 100, though variable with the kind of the alkylene. Among other alkylene glycols mentioned above, polyethylene glycol and polypropylene glycol prove to be preferable. It is particularly preferable to use polyethylene glycol having a degree of polymerization in the range of from 20 to 90 or polypropylene glycol having a degree of polymerization in the range of from 10 to 50.

The polymer for this invention is as already described.

The substrate is used in any of various forms such as, for example, a sheet, a tube (inclusive of a hollow fiber), and fibers.

Though the method to be employed for the production of the medical material of this invention is not particularly restricted, the following method can be used preferably. Specifically, this method comprises a step of forming a covalent bond between the functional group of a higher alcohol and/or a higher alcohol macromer and part of the functional group of a polymer and a step of forming a covalent bond between part of the functional group of the polymer and the functional group of the substrate. These steps may be carried out either simultaneously or sequentially in any desired order.

When a higher alcohol and/or a higher alcohol macromer containing amino groups at the opposite terminals, for example, a polymer containing an epoxy group and the higher alcohol macromer form a graft copolymer through the medium of the epoxy group contained in the polymer or a copolymer containing an epoxy group and a carboxyl group and a higher alcohol and/or a higher alcohol macromet form a macromolecular derivative in the form of a graft copolymer through the medium of the carboxyl group of the polymer.

For the reaction resulting in the formation of the graft copolymer, any of the known conventional methods of synthesis can be used.

Now, this invention will be described more specifically below with reference to working examples.

EXAMPLE 1

(1) Synthesis of linolic acid macromer

A solution of 20.0 g of linolic acid in 70 ml of dry benzene was placed in a flask and kept swept therein with nitrogen for displacement of the entrapped air and 14.8 g of phosphorus pentachloride was added meanwhile thereto as divided in five split portions. The resultant reaction mixture was stirred at normal room temperature for 12 hours and then refluxed for two hours. Then, the reaction solution was distilled to expel benzene and the products of a secondary reaction, i.e. phosphoryl trichloride and hydrogen chloride and the residue was subjected to vacuum distillation to produce 14.0 g of linolic acid chloride (boiling point 155° C./1.5 mmHg; yield 76%).

In a flasks 50.4 g of polyethylene glycol diamine (a product of a molecular weight of 4,114; marketed by Toray Ltd. under product code of "PGD-40"), 1.48 g of triethyl amine, and 120 ml of dichloromethane were placed and kept swept with nitrogen and a solution of 3.66 g of linolic acid chloride in 70 ml of dichloromethane was added dropwise thereto over a period of 30 minutes. Then, the reaction mixture was left gradually warming to normal room temperature and, at the same times stirred for two hours. The resultant reaction solution was filtered to remove triethyl amine as the product of a secondary reaction and subjected to vacuum distillation to expel triethyl amine and dichloromethane. The residue was dissolved in 100 ml of chloroform and washed gently with 100 ml of water. The organic layer consequently formed was separated, dried with anhydrous soidum sulfate, and concentrated. When the concentrate was purified by flush chromatography (decomposing solution: chloroform/methanol V/V) using Wako C-300, 13.7 g of a purified product (macromet of linolic acid) was obtained (yield 26%).

The structure of the purified product was identified by the IR method and the $^1$H-NMR method and the perfect absence of linolic acid and PGD-40 from the purified product was confirmed by liquid chromatography (GPC modes dissolving solution THF).

The results of the tests described above are shown below.
IR method:
  1650 $cm^{-1}$ - expansive motion of amide carbonyl
  1540 $cm^{-1}$ - angular motion of amide NH
  1100 $cm^{-1}$ - expansive motion of ether
$^1$H-NMR method:
  $\delta$0.3 ppm - linolic acid - $CH_3$
  $\delta$1.3 ppm - linolic acid - $CH_2$—
  $\delta$3.7 ppm - polyethylene glycol - $OCH_2CH_2O$
  $\delta$5.3 ppm - olefin linolate - CH=CH—
GPC method:
  Volume of purified product retained 11.4 ml
  PGD-40 12.6 ml
  Linolic acid 15.1 ml (2) Synthesis of copolymer A polymerization tube made of glass was charged with 0.15 part by weight of azo-bis-isobutylonitrile as a polymerization initiator, 7.5 parts by weight of methyl methacrylate, 15 parts by weight of glycidyl methacrylate, 6 parts by weight of 3-methacryloxypropyl tris(methoxyethoxy)silane (produced by Chisso Corp.), and 1.5 parts by weight of methacrylic acid. The polymerization tube was cooled and solidified in liquefied nitrogen, alternately evacuated of air and displaced with nitrogen repeatedly, and then sealed tightly. The sealed tube containing the reaction mixture was heated in a constant temperature bath at 60° C. for 50 minutes. Thereafter, the tube was cooled and opened. The content was dissolved in THF and reprecipitated with methanol, to obtain a white copolymer.

The copolymer was dissolved in methylethyl ketone and titrated with a 0.01N perchloric acid/acetic acid solution using triethyl trimethyl ammonium bromide as a catalyst and crystal violet as an indicator to determine an epoxy equivalent and find the composition of glycidyl methacrylate. The yield was found to be 52.9% by weight.

(3) Reaction of linolic acid macromer with copolymer

In a flask, 4.00 g of the copolymer obtained in (2), 0.718 g of dicyclohexyl carbodiimide, and 100 ml of a mixed solvent of carbon tetrachloride/acetonitrile (1:1 v/v) were placed, stirred at normal room temperature for 60 minutes as kept swept with nitrogen and, after thorough solution, a solution of 12.0 g of the linolic acid macromer obtained in (1) in 20 ml of carbon tetrachloride/acetonitrile (1:1 v/v) was gradually added dropwise thereto. Then, the resultant mixture was stirred at normal room temperature for 60 minutes and further stirred at 60° C. for 60 minutes. The reaction product was cooled to normal room temperature. The content of the flask was passed through a glass filter. When the filtrate was gently distilled to expel the solvent, there was obtained a yellow highly viscous crude product.

The crude product and 200 ml of methanol added thereto were stirred at normal room temperature for about 30 minutes, and subjected to centrifugal separation. The supernatant was removed by decantation. The procedure was repeated twice more. When the final residue was subjected to vacuum drying, there was obtained 9.63 g of a macromolecular derivative.

(4) Graft polymerization of macromolecular derivative to regenerated cellulose

In 100 ml of an aqueous 0.3 (w/v) % sodium hydroxide solution, 300 regenerated cellulose membranes (0.2 mm in thickness) were immersed for 30 minutes. Then, the regenerated cellulose membranes were immersed in an aqueous acetone solution containing the macromolecular derivative obtained in (3) in a concentration of 0.5 (w/v) % and left reacting therein at normal room temperature for 24 hours.

After the reaction was completed, the regenerated cellulose membranes were removed from the aqueous solution, washed with acetone, ethanol, and distilled water sequentially in the order mentioned, to produce regenerated cellulose membranes A having the macromolecular derivative graft polymerized to the surface thereof.

(5) Preparation of dialyzer using regenerated cellulose membranes

A hollow fiber bundle 5 was formed of 340 hollow fibers of regenerated cellulose of cuprammonium measuring about 200 μm in inside diameter, about 224 μm in outside diameter, and 14 cm in available length and obtained in (4). The hollow fiber bundle 5 was inserted in a cylinder proper 4 as illustrated in FIG. 1 and the opposite ends of the hollow fiber bundle were immobilized in place with discs 6, 7 of a polyurethane type potting agent. Headers 10, 11 were attached to the opposite ends and fixed with caps 12, 13, to complete a dialyzer (artificial kidney) 1. The membranes had an inside surface of 300 cm². In the dialyzer illustrated in FIG. 1, a cylindrical body 4 was provided near the opposite terminal parts thereof with an inlet tube 2 and an outlet tube 3 for passage of a fluid for dialysis.

(6) Deposition of vitamin E on regenerated cellulose membrane

A 1,1,2-trichloro-1,2,2-trifluoroethane solution of vitamin E was prepared by dissolving 5.0 g of vitamin E (-tocopherol) in 100 ml of 1,1,2-trichloro-1,2,2-trifluoroethane. A syringe was connected to one end of the dialyzer and the other end of the dialyzer was susbmerged in the vitamin E solution. The plunger of this syringe was operated to introduce the vitamin E solution into the dialyzer to capacity. Then, the dialyzer was pulled out of the vitamin E solution, emptied of the vitamin E solution, and dried by means of an aspirator capable of supplying a current of air at 25° C. It was further left standing in an oven at 60° C. for one hour. It was subsequently treated in an autoclave at 115° C. for 30 minutes to complete a dialyzer A of this invention.

Control

A dialyzer B for comparison was prepared by following the procedure of Example, excepting a cellulose membrane B which had undergone a treatment for coating with vitamin E and none of the treatments (1) to (4) mentioned above was used instead as a regenerated cellulose membrane.

Test for extracorporeal circulation

The dialyzers A and B and a dialyzer C packed with untreated regenerated cellulose were tested for performance in extracorporeal circulation.

A rabbit was fastened as laid on the back to a Kitajima's stationary bed. Then, the hair in the region selected for surgery was clipped with an electric clipper and thoroughly wiped with a wad impregnated with alcohol. The throat was cut open along the median line from below the jaw through the clavicle with a scissors, the fascia consequently exposed was opened, and the right (left) catroic artery and then the left (right) facial vein were excoriated advertently so as to avoid injuring the nerve, the branched blood vessel, and the neighboring tissue. An indwelling catheter (produced by Terumo K.K.) filled with a 1 IU/ml heparin-added physiological saline solution and stoppered with a mixture-dispensing rubber cap was inserted into the artery mentioned above and tied thereto. A similar catheter was inserted in the vein mentioned above and tied thereto. An experimental circuit incorporating therein a given dialyzer, A to C, was laid through the rabbit 20 prepared as described above. To be specific, a catheter 21 connected to the artery of the rabbit 20 was connected on the free end to a pump 22 and a chamber 23 and the vein of the rabbit 20 were interconnected through the medium of a catheter 25. The pump 22 and the dialyzer 1 were interconnected through the medium of a tube 26, which was connected to an in 27 side of a manometer. Further, the dialyzer 1 and the chamber 23 connected to an out 24 side of the manometer were interconnected through the medium of a tube 28. The inlet and the outlet of the dialyzer for passage of the fluid for dialysis were interconnected through the medium of a tube 29, which was furnished with a pump 30 and immersed in a water bath kept at 37° C.

The circuit so constructed was cleaned by being primed with 100 ml of 1 IU/ml heparin-added physiological saline solution. The extracorporeal circulation of blood was carried out at a rate of 10 ml/min. Absolutely no anticoagulant was used in the blood in circulation. The blood in circulation was sampled in a fixed size of 1 ml after the intervals of 5, 10, 15, 20, 30, 45, 60, and 120 minutes following the start of the circulation. Each sample was treated with a 1.5% EDTA-2Na physiological saline solution to be proofed against coagulation and then analyzed with an ELT-8 (produced by Orth Instument Corp.) to find the number of blood cells.

The data consequently obtained concerning the count of white blood cells (WBC), the count of blood platelets (PLT), and the hematocrit value (HCT) are shown in Tables 1 to 3. Specifically, Table 1 shows the data on the experimental circuit using the dialyzer A, Table 2 the data on the experimental circuit using the dialyzer B, and Table 3 the data on the experimental circuit using the dialyzer C. The count of blood platelets was subjected to Ht value correction in accordance with the following numerical expression and reported in the magnitude of Ht value found immediately before the start of circulation.

i $Cx = Co \times Htx/Hto$ wherein $Cx$ is a corrected value, $Co$ is a found value, $Htx$ is an initial Ht value, and $Hto$ is a Ht value existing at the time the Co value was obtained.

The amounts of vitamin E retained initially on the regenerated celluloses A and B were determined by the HPLC analysis. The conditions for the HPLC analysis were as shown in Table 4. The amount of vitamin E eluted in the circulating blood was determined by sampling 1 ml of the circulating blood plasma, mixing the sample with 1 ml of ethanol for 30 seconds, then mixing the resultant mixture with 5 ml of hexane for one minute, and centrifuging the final mixture at a rate of 1,500 rpm for five minutes thereby separating and extracting the vitamin E emanating from the sample. The ratio of vitamin E elution (=(Amount of eluted vitamin E/Amount of vitamin E initially deposited) ×100) was calculated by the use of the found values.

TABLE 1

| Time min | WBC /mm³ | WBC PIC (%) | PLT ×10⁴ /mm³ | PLT PIC (%) | HCT % | HCT PIC (%) | Ratio of vitamin E elution wt % |
|---|---|---|---|---|---|---|---|
| Initial | 29.2 | 100 | 31.8 | 100 | 39.7 | 100 | 0 |
| 5 | 24.5 | 83.5 | 25.9 | 81.0 | 39.9 | 100.5 | |
| 10 | 24.8 | 85.2 | 25.9 | 81.7 | 39.6 | 99.7 | |
| 15 | 28.5 | 98.1 | 25.9 | 81.9 | 39.5 | 99.5 | |
| 20 | 29.0 | 102.2 | 25.2 | 81.5 | 38.6 | 97.2 | |
| 30 | 30.2 | 107.2 | 24.4 | 79.5 | 38.3 | 96.5 | 0.1 |
| 45 | 33.0 | 122.6 | 22.0 | 75.0 | 36.6 | 92.2 | |
| 60 | 35.3 | 132.3 | 22.7 | 78.1 | 36.3 | 91.4 | 0.5 |
| 120 | 40.7 | 153.3 | 21.8 | 75.4 | 36.1 | 90.9 | 0.5 |

TABLE 2

| Time min | WBC /mm³ | WBC PIC (%) | PLT ×10⁴/mm³ | PLT PIC (%) | HCT % | HCT PIC (%) | Ratio of vitamin E elution wt % |
|---|---|---|---|---|---|---|---|
| Initial | 6200 | 100 | 61.3 | 100 | 43.3 | 100 | 0 |
| 5 | 5710 | 92.1 | 57.3 | 93.5 | 39.4 | 91.0 | |
| 10 | 4030 | 90.5 | 56.3 | 91.8 | 39.9 | 92.1 | |
| 15 | 4220 | 75.2 | 54.8 | 89.4 | 39.2 | 90.5 | |
| 20 | 5200 | 83.9 | 53.4 | 87.1 | 39.1 | 90.3 | |
| 30 | 5140 | 84.5 | 50.6 | 82.5 | 39.7 | 91.7 | 80.0 |
| 45 | 5450 | 96.4 | 46.7 | 76.1 | 39.5 | 91.2 | |
| 60 | 5930 | 106.7 | 46.1 | 75.2 | 38.8 | 89.6 | 86.0 |
| 120 | 7380 | 119.0 | 42.4 | 69.2 | 39.3 | 90.7 | 89.0 |

TABLE 3

| Time min | WBC /mm³ | WBC PIC (%) | PLT ×10⁴ /mm³ | PLT PIC (%) | HCT % | HCT PIC (%) | Ratio of vitamin E elution wt % |
|---|---|---|---|---|---|---|---|
| Initial | 8100 | 100 | 86.4 | 100 | 44.4 | 100 | |
| 5 | 4230 | 52.2 | 79.8 | 92.4 | 39.3 | 89.9 | |
| 10 | 3850 | 47.5 | 76.8 | 88.9 | 39.2 | 88.3 | |
| 15 | 4100 | 50.6 | 73.2 | 84.7 | 41.2 | 92.8 | |
| 20 | 4520 | 55.8 | 71.4 | 82.6 | 40.3 | 90.8 | |
| 30 | 6820 | 84.2 | 59.8 | 78.0 | 39.4 | 86.5 | |
| 45 | 6870 | 84.8 | 66.7 | 77.2 | 38.9 | 87.6 | |
| 60 | 8790 | 108.5 | 44.8 | 59.2 | 38.9 | 87.6 | |
| 120 | 11250 | 142.2 | 42.7 | 55.0 | 39.7 | 89.4 | |

TABLE 4

| | |
|---|---|
| Apparatus: | Twincle (manufactured by Nippon Bunko K.K.) |
| Column: | Toso-TSK Gel Amido-80 4.6 × 25 mm |
| Moving bed: | n-hexane: isopropanol (95:5) mixed solution |
| Rate: | 1.5 ml/min |
| Determination: | UY monitor 292 nm |
| Pressure: | 75 kg/cm² |
| Sample solution: | ethanol solution |
| Injection amount: | 10 µl |

It is clearly noted from Tables 1 to 3 that the dialyzer A embodying this invention manifested stable biocompatibility as evinced by only a small elution of the vitamin E in the circulating blood because the vitamin E was deposited through the medium of a macromer possessed of a hydrophobic moiety, whereas the dialyzer B embodying the conventional technique showed gradual decline of bioadaptability with the elapse of time because the vitamin E was physically deposited simply in the foam of a coating and, therefore, was highly susceptible of elution.

EXAMPLE 2

(1) Synthesis of oleyl alcohol macromer

In 50 ml of dioxane, 20.00 g of polyethylene glycol monooleyl ether (average molecular weight 4,268) obtained by addition of ethylene oxide to an oleyl alcohol in the presence of an alkali catalyst and 1.90 g of triethyl amine were dissolved. The resultant solution and a solution of 1.85 g of p-toluenesulfonyl chloride in 10 ml of dioxane slowly added dropwise thereto were left reacting at 60° C. for two hours. The reaction product was refined by being dissolved with 200 ml of acetone added thereto, then cooled to 0° C., and left standing to allow sedimentation of the product aimed at. Then, a solution of 6.50 g of the product mentioned above in 30 ml of DMF and 0.55 g of potassium phthalimide added thereto were left reacting at 90° C. for two hours. The reaction product was refined by being dissolved with 60 ml of acetone added thereto, then cooled to 0° C., and left standing to allow sedimentation of the product aimed at. Subsequently, a solution of 6.00 g of the product mentioned above in 30 ml of ethanol and 1.00 g of hydrazinc hydrate added thereto were left reacting as refluxed for two hours. The reaction product was refined by being dissolved with 60 ml of acetone added thereto, then cooled to 0° C., and left standing to allow sedimentation of the product aimed at. Consequently, 5.20 g of an oleyl alcohol macromer possessed of amino groups at the terminals thereof was obtained.

(2) Synthesis of copolymer

A polymerization tube made of glass was charged with 0.15 part by weight of azo-bis-isobutylonitrile as a catalyst, 7.5 part by weight of methyl methacrylate, 15 parts by weight of glycidyl methacrylate, 6 parts by weight of 3-methaeryloxypropyl tris(methoxyethoxy) silane (produced by Chisso Corporation), and 1.5 parts by weight of methacrylic acid, cooled and solidified with liquefied nitrogen, alternately subjected to evacuation of air by a vacuum pump and displacement of the entrapped air with nitrogen repeatedly, and thereafter sealed tightly. In a constant temperature bath, the polymerization tube was heated at a prescribed temperature for a prescribed time. It was cooled and opened to remove the content. The polymerization mixture was dissolved in tetrahydrofuran and reprecipitated in methanol. Consequently, a white polymer was obtained.

Similarly, a copolymer containing no methacrylic acid was synthesized.

The copolymer was dissolved in methylethyl ketone. The solution was titrated with a 0.01N perchloric acid/acetic solution in the presence of ethyl bromide trimethyl ammonium as a catalyst and crystal violet as an indicator to find an epoxy equivalent and the composition of glycidyl methacrylate (Table 5).

TABLE 5

| Charged monomer | Copolymer Nov. | Polymerization Temperature (°C.) | Polymerization time (min) | Content of glycidyl methacrylate (wt %) |
| --- | --- | --- | --- | --- |
| A | 1 | 60 | 50 | 52.9 |
| B | 2 | 60 | 50 | 52.7 |

A: MMA/GMA/MPTMS/MA = 7.5/15/6/1.5 (wt. ratio)
B: MMA/GMA/MPTMS = 7.5/15/7.5 (wt. ratio)
MMA: methyl methacrylate
GMA: glycidyl methacrylate
MPTMS: 3-methacryloxypropyltris (methoxyethoxy) silane
MA: methacrylic acid (3) Reaction of oleyl alcohol macromer with copolymer In a flask, 4.00 g of the aforementioned copolymer No. 1, 0.718 g of dicyclohexylcarbodiimide, and 100 ml of a mixed solvent of carbon tetrachloride/acetonitril (1:1 by volume) were stirred as kept swept with nitrogen for 60 minutes. The resultant solution and a solution of 9.92 g of the oleyl alcohol macromer in 20 ml of carbon tetrachloride/acetonitrile (1:1 by volume) gradually added dropwise thereto were stirred at room temperature for 60 minutes and further stirred at 60° C. for 60 minutes. The content of the flask was cooled to normal room temperature and then passed through a glass filter. When the filtrate was distilled gently to expel the solvent by evaporation, there was obtained a yellow highly viscous crude product.

The crude product and 200 ml of methanol added thereto were stirred at normal room temperature for about 30 minutes untillumps ceased to exist. The resultant solution was centrifuged and the supernatant was removed by decantation. This procedure was repeated twice more. The final residue was dried under a vacuum, to produce 8.75 g of a macromolecular derivative.

(4) Bonding of macromolecular derivative to regenerated cellulose membrane

The macromolecular derivative was bonded to the surface of regenerated cellulose as follows.

First, 0.3 g of regenerated cellulose membrane (0.2 mm in membrane thickness) was kept immersed in 100 mm of an aqueous 0.5 (W/V) % sodium hydroxide solution for 30 minutes. Then, the cellulose membrane was immersed in an acetone solution of 0.5 (W/V) % of the macromolecular derivative and left reacting therein at normal room temperature for 24 hours. After the reaction was completed, the regenerated cellulose membrane was taken out of the solution and thoroughly washed with acetone, ethanol, and distilled water sequentially in the order mentioned, to obtain a sample 1 of the medical material embodying this invention.

Controls 2 and 3

A mixture of 0.04 g of pyridine with 30 ml of dry dioxane was prepared. Then, 0.90 g of linolic acid was introduced by the use of this mixture into a flask. The resultant mixture in the flask was stirred as kept swept with nitrogen at 80° C. for 30 minutes. The content of the flask and a solution of 3.00 g of the copolymer No. 2 in 70 ml of dry dioxane added thereto were stirred at 80° C. for six hours. The resultant reaction mixture was cooled to normal room temperature and subjected to gentle distillation to expel the solvent by evaporation. Consequently, a light brown highly viscous crude product was obtained. The crude product and 100 mm of methanol added thereto were stirred at normal room temperature for about 30 minutes (until lumps ceased to exist) and subjected to centrifugal separation. The supernatant was removed by decantation. When this procedure was repeated twice more and the final residue was subjected to vacuum drying, 3.05 g of a macromolecular derivative was obtained. A sample 2 (Control 2) was obtained by bonding the macromolecular derivative to regenerated cellulose membrane by following the procedure of Example.

A regenerated cellulose membrane was used as Sample 3 (Control 3).

Evaluation Test 1

The samples of Example 2 and Controls 2 and 3 were tested for change of correction value in accordance with the original Mayer method indicated below. The results of the test are shown in Table 6.

Each sample was preparatorily brought to an equilibrium state of sorption by immersion in physiological saline solution. The sample was gently wiped to remove water from the surface and trimmed into a small piece 20 $cm^2$ in surface area. The cut sample was placed in a plastic blood collecting tube and 1 ml of the serum extracted from an adult dog was automatically added to the cut sample in the tube. The contents of the tube were kept at 370° C. for three hours to activate the cut sample to determine the change in the correction value CH50 (correction value determined by the 50% hemolysis method) and calculate the ratio of consumption.

TABLE 6

| Sample | Consumption rate of CH50 |
| --- | --- |
| Example 2 (Sample 1) | 13.5 |
| Control 2 (Sample 2) | 14.2 |
| Control 3 (Sample 3) | 35.7 |

It is clearly noted from Table 6 that the medical material of this invention brings about a very small decrease of the correction value CH50 in the serum as compared with the untreated sample.

Evaluation Test 2

By the use of a polypropylene syringe preparatorily containing an aqueous 3.8% sodium citrate solution (⅑ of the volume of the blood to be subsequently collected), the venous blood of a healthy man was extracted. The blood was transferred into a polypropylene test tube by causing it to flow gently down on the inner wall of the test tube and then centrifuged at 800 r.p.m. for five minutes. The platelet rich blood plasma (PRP) in the supernatant was collected and diluted with a dilute aqueous 3.8% sodium citrate solution (1/10 of the volume of a lactic acid Ringer's solution) to prepare a platelet suspension. This plate suspension was found to contains 66,000 platelets per $mm^2$. On each sample (1 $cm^2$) from Example 1 and Controls 2 and 3, 0.2 ml of the platelet suspension was placed in a thickness of 2 mm and brought into contact at normal room temperature for 30 minutes. After the elapse of a prescribed time, the sample was gently washed with a dilute 3.8% sodium citrate solution. Then, the sample was placed in a 2.5% glutar aldehyde/ lactic acid Ringer's solution and left standing overnight in a cool place to be fixed. The fixed sample was gently washed with a dilute 3.8% sodium citrate solution, subjected to stepped dehydration with an ethanol series (sequential 10 minutes treatment in ethanol solutions having ethanol contents of 50%, 60%, 70%, 80%, 90%, 95%, 100%, and 100%), dried with a current of air, and observed under a scanning electron microscope (produced by Nippon Denshi K.K. and marketed under product code of "JSM-840"). The evaluation was made on the basis of the number of platelets adhering to a sample area of 0.07 mm$^2$ and the change in form. The change in form was classified under the following three types.

Type I: The platelets transformed from their normal shape of discs into spheres with three to four protruding pseudopodia and suspected to be bound relatively weakly to the surface of a given sample.

Type II: The platelets transformed to the extent of protruding more than several pseudopodia and expanding cells to half the size of pseudopodia and suspected to be bound strongly to the surface of a given sample.

Type III: The platelets transformed to the extent of expanding thin cells to more than half of the length of pseudopodia, with the cells substantially completely spread out in a substantially circular pattern and suspected to be bound thoroughly to the surface of a sample.

The results are shown in Table 7.

TABLE 7

| Sample | Form of platelet | | | Number of platelet attached |
| --- | --- | --- | --- | --- |
| | type I | type II | Type III | number/0.07 mm2 |
| Example 1 | 66.7 | 25.6 | 7.7 | 78 |
| Control 2 | 62.3 | 31.2 | 6.5 | 93 |
| Control 3 | 51.9 | 37.2 | 10.9 | 478 |

It is clearly noted from Table 7 that the medical materials of this invention exhibit ideal resistance to thrombosis as compared with the untreated samples and the samples having a fatty acid fixed thereon.

What is claimed is:

1. A medical material which comprises an oil-soluble vitamin hydrophobically bound to a hydrophobic moiety containing macromet, said hydrophobic bond between said oil-soluble vitamin and said hydrophobic moiety occurring in the presence of water, and said macromer is bound to the surface of a polymeric substrate, wherein said macromer is bound to the surface of the polymeric substrate via a copolymer, wherein the copolymer contains a reactive group, which reactive group is covalently bonded with a functional group contained on the surface of said polymeric substrate.

2. A medical material according to claim 1, wherein said hydrophobic moiety is at least one side chain selected from the group consisting of fluorine side chain, silicone side chain, and alkyl side chain.

3. A medical material according to claim 1, wherein said hydrophobic moiety has an average molecular weight in the range of from 100 to 5,000.

4. A medical material according to claim 1, wherein said reactive group capable of forming a covalent bond with said polymer is at least one member selected from the class consisting of epoxy group, carboxyl group, carboxylic ester group, and aldehyde group.

5. A medical material according to claim 1, wherein said copolymer containing a reactive group capable of forming a covalent bond with said polymer has an average molecular weight in the range of from 500 to 500,000.

6. A medical material according to claim 1, wherein said oil-soluble vitamin is vitamin E.

7. A medical material according to claim 1, wherein said polymer containing said functional group is a polymer containing at least one member selected from the class consisting of hydroxyl group, amino group, carboxyl group, epoxy group, and aldehyde group.

8. A medical material according to claim 7, wherein said polymer is a polymer containing a hydroxyl group.

9. A medical material according to claim 8, wherein said polymer containing a hydroxyl group is regenerated cellulose or a cellulose derivative.

* * * * *

UNITED STATES PATENT AND TRADEMARK OFFICE
CERTIFICATE OF CORRECTION

PATENT NO. : 5,489,303
DATED : February 6, 1996
INVENTOR(S) : Masatomi SASAKI et al It is certified that error appears in the above-indentified patent and that said Letters Patent is hereby corrected as shown below:

In Column 3, line 17, delete "aidehyde" and insert -- aldehyde --.

In Column 3, line 19, delete "aidehyde" and insert -- aldehyde --.

In Column 3, line 47, delete "aidehyde" and insert -- aldehyde --.

In Column 4, line 54, after "copolymer is" insert -- preferably contains --.

In Column 4, line 55, delete "aidehyde" and insert -- aldehyde --.

In Column 5, line 5, delete "eerie" and insert -- ceric --.

In Column 5, line 13, delete "macromet" and insert -- macromer --.

In Column 7, line 30, delete "sheleton" and insert -- skeleton --.

In Column 7, lines 60-61, delete "macromet" and insert -- macromer --.

In Column 8, line 17, delete "flasks" and insert -- flask, --.

In Column 8, line 25, delete "times" and insert -- time --.

In Column 8, line 35, delete "macromet" and insert -- macromer --.

In Column 11, line 7, delete "i".

In Column 12, line 63, delete "3-methaeryloxypropyl" and insert -- 3-methacryloxypropyl --.

In Column 13, line 54, delete "100 mm" and insert -- 100 ml --.

In Column 14, line 9, delete "100 mm" and insert -- 100 ml --.

In Column 14, line 67, delete "aidehyde/" and insert -- aldehyde/ --.

UNITED STATES PATENT AND TRADEMARK OFFICE
CERTIFICATE OF CORRECTION

PATENT NO. : 5,489,303
DATED : February 6, 1996
INVENTOR(S) : Masatomi Sasaki, et. al.

It is certified that error appears in the above-indentified patent and that said Letters Patent is hereby corrected as shown below:

In Column 16, line 4, delete "macromet" and insert -- macromer --.

Signed and Sealed this

Thirtieth Day of July, 1996

Attest:

BRUCE LEHMAN

Attesting Officer

Commissioner of Patents and Trademarks